(12) United States Patent
Friberg et al.

(10) Patent No.: US 7,461,654 B2
(45) Date of Patent: Dec. 9, 2008

(54) DEVICE AND METHOD FOR GENERATION OF RESPIRATIONAL AIR

(75) Inventors: Harri Friberg, Buchs (CH); Jakob Däscher, Buchs (CH)

(73) Assignee: imt medical ag, Vaduz (LI)

( * ) Notice: Subject to any disclaimer, the term of this patent is extended or adjusted under 35 U.S.C. 154(b) by 400 days.

(21) Appl. No.: 10/535,016

(22) PCT Filed: Nov. 20, 2002

(86) PCT No.: PCT/IB02/04838

§ 371 (c)(1),
(2), (4) Date: Oct. 31, 2005

(87) PCT Pub. No.: WO2004/045695

PCT Pub. Date: Jun. 3, 2004

(65) Prior Publication Data

US 2006/0120886 A1    Jun. 8, 2006

(51) Int. Cl.
*A61M 16/00* (2006.01)
(52) U.S. Cl. ............ 128/204.15; 128/204.16; 128/204.18
(58) Field of Classification Search ............ 128/204.15–204.18, 204.26, 205.12, 204.23, 128/911, 912
See application file for complete search history.

(56) References Cited

U.S. PATENT DOCUMENTS

| | | | | |
|---|---|---|---|---|
| 2,955,877 A | * | 10/1960 | Ecal | 406/47 |
| 3,301,255 A | * | 1/1967 | Thompson | 128/200.18 |
| 3,990,442 A | * | 11/1976 | Patneau | 128/203.16 |
| 4,080,103 A | | 3/1978 | Bird | |
| 4,257,415 A | * | 3/1981 | Rubin | 128/200.21 |
| 5,222,489 A | * | 6/1993 | Garoutte | 128/204.15 |
| 5,299,565 A | * | 4/1994 | Brown | 128/200.21 |
| D383,838 S | * | 9/1997 | Solano | D24/110 |
| 5,722,393 A | * | 3/1998 | Bartel et al. | 128/204.15 |
| 5,752,506 A | * | 5/1998 | Richardson | 128/204.18 |
| 6,729,333 B2 | * | 5/2004 | Barnett et al. | 128/207.13 |
| 7,188,623 B2 | * | 3/2007 | Anderson et al. | 128/207.16 |

* cited by examiner

*Primary Examiner*—Steven O Douglas
(74) *Attorney, Agent, or Firm*—Matthew B. Dernier, Esq.; Gibson & Dernier LLP

(57) ABSTRACT

The invention relates to a device and a method for the generation of respirational air. The device according to the invention makes it possible to dehumidify air optimally. The dehumidification problem is achieved with a tapering passage, in particular with a nozzle. The nozzle is contained in a tube in which the mixture of air and water flows. A pressure which is higher on one side and which leads to a local increase in the flow rate in the nozzle and to a lower temperature prevails in the nozzle. These circumstances result in the water further condensing out of the air in the nozzle. The water which is condensed out is entrained by the air stream and can be separated off in a water separator connected directly after the nozzle, even before the gas or the air (after the nozzle) can become saturated again.

6 Claims, 3 Drawing Sheets

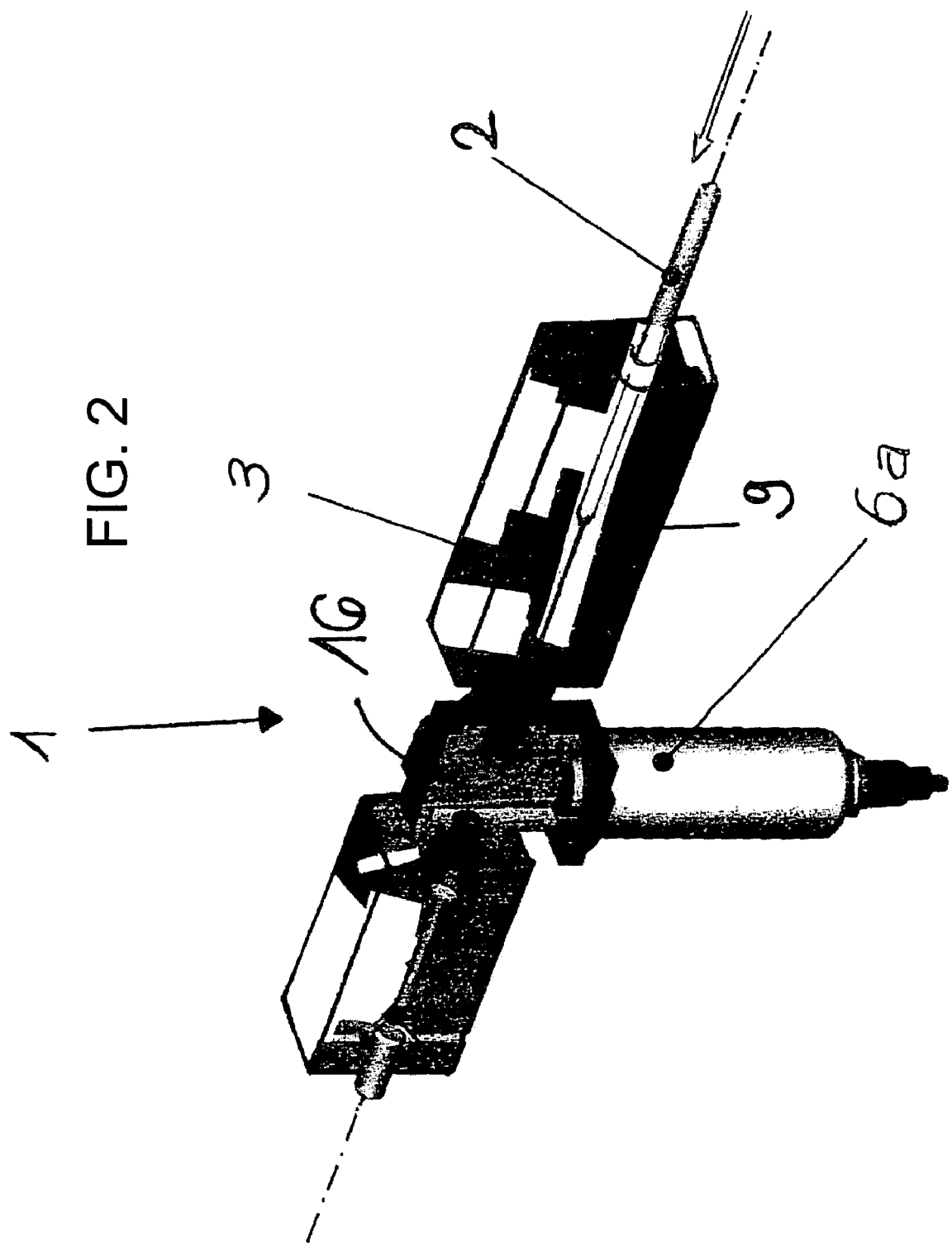

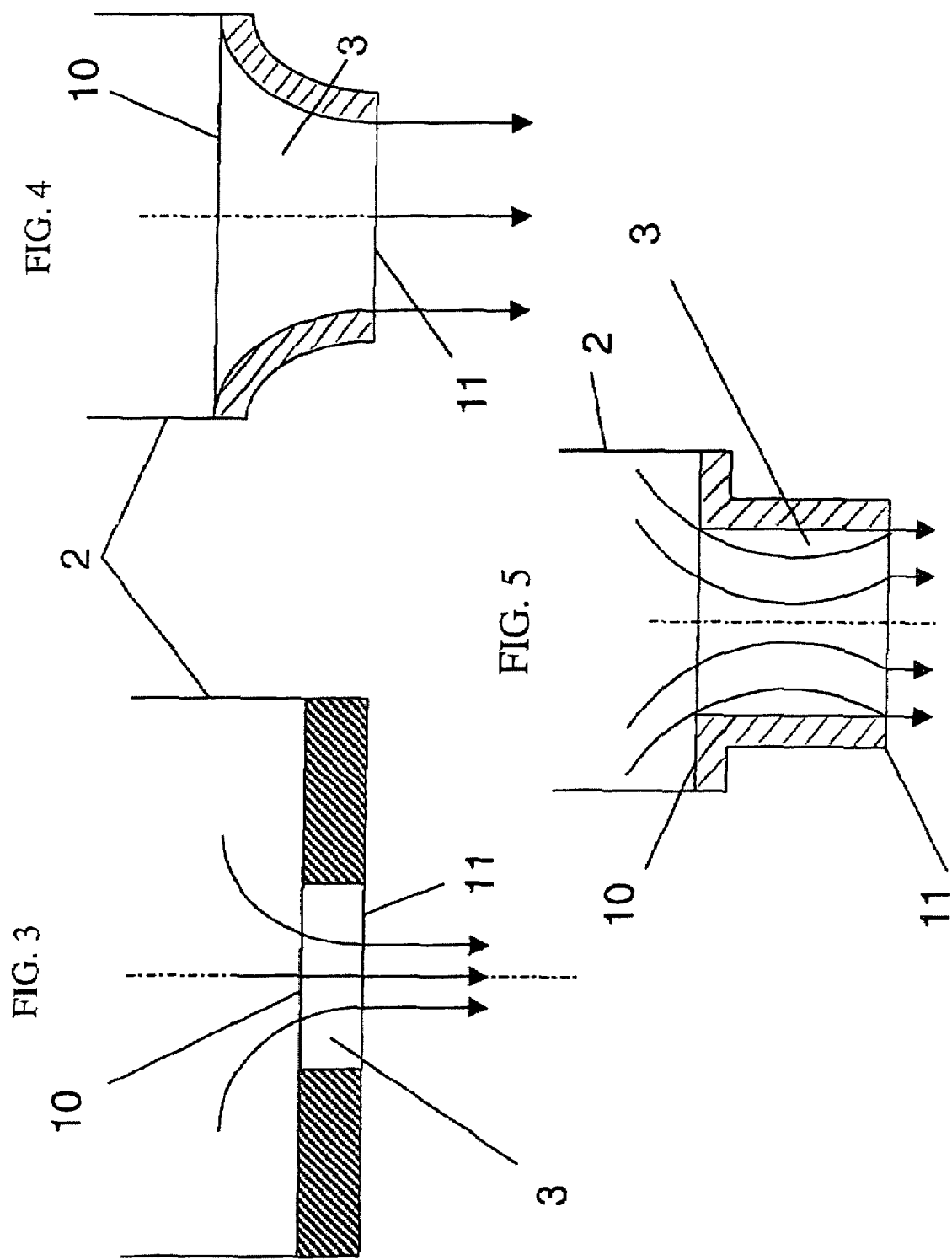

DEVICE AND METHOD FOR GENERATION OF RESPIRATIONAL AIR

BACKGROUND

The invention relates to a device and a method for the generation of respirational air.

There have been several efforts to date to generate dry respirational air. It is known that, if gas or air is compressed in a space, its moisture absorptivity is high and, on cooling the air, for example in a storage container, a part of the absorbed moisture can condense, which is undesired. Furthermore, only a certain atmospheric humidity is desired for respiration. Respirational air from a compressor must therefore be dehumidified both for technical reasons and for health reasons.

The prior art includes devices which would partly solve the above-mentioned dehumidification problem via mechanical separators having microfilters, by heat treatment of the air or with the aid of chemical drying systems (e.g. with salt).

The inventor recognized that the known systems are disadvantageous with respect to the following: The devices to date achieved complicated or insufficient dehumidification of respirational air. In many of them, the separation of water from the gas or the air can be realized only partly. This means that optimum atmospheric humidity has been achieved to date only with great effort or not at all by the known methods.

SUMMARY

In the context of the invention, respirational air is to be understood as meaning that gas or air mixture which can be supplied mechanically to a patient.

In the context of the invention, moisture is to be understood as meaning water or another liquid or liquid mixture in the liquid or gaseous or air-like state of aggregation.

Nozzle shape is to be understood as meaning the shape of the outflow nozzle, which may have various possible designs.

In the context of the invention, tapering passage is to be understood as meaning, in terms of a constricted flow, in particular an aperture or a nozzle in a tube, in which, owing to higher pressure on one side, a local increase in the flow rate is produced on the one hand and a local, lower temperature of the respirational air after the tapering passage in relation to the temperature before the tapering passage is produced on the other hand.

It is an object of the invention to develop a device and a method in which the respirational air is generated with good quality and by means of which the moisture content can achieve an optimum, without having to make too great an effort.

This object is achieved by i) a tapering passage in a tube of the device having a nozzle and subsequent water separation by means of a conventional water separator. The nozzle may also be mounted after the water separator.

ii) the physical effect whereby, in the region of the nozzle, the mixture of gas or air and water is converted, owing to the temperature drop after the nozzle—which arises because of the pressure drop after the taper—into a physical state in which the water can be more readily condensed out or separated from the gas or from the air.

iii) the effect whereby the water which has condensed out can be entrained by the air stream and separated off immediately after the nozzle in a water separator even before the respirational air can become saturated again with the water which is condensed out.

iv) before the mixture of gas or air and water arrives at the nozzle, it is first cooled in a radiator by fans in order to reach a lower temperature.

As a result of the process for the dehumidification of respirational air described above, the following improvements are achieved in the following steps: (i) owing to the tapering passage (with a nozzle) in the tube, there is a higher pressure before this nozzle and an increase in the flow rate in the taper and thereafter a pressure drop, as a result of which the temperature of the gas or air mixture decreases correspondingly, permitting optimum water separation.

(ii) The pressure required by the separation process is measured, for example, in a test setup of manometers, and the temperature by temperature sensors in the tube.

The fundamental concept of the invention can be achieved in various embodiments.

The nozzle taper, which plays the most determining role in the case of the device according to the invention may have various forms which can influence the rate of flow.

If the nozzle has a sharp-edged form, the flow rate coefficient is high (0.97 ϕ). In this possible embodiment, the widths of entrance and exit are the same.

In another variant, the nozzle form is rounded, the passage is fairly long and the width of the entrance is approximately twice as great as that of the exit, and accordingly an even higher flow rate (0.97-0.99 ϕ) is produced.

As an alternative, the nozzle may have a cylindrical or polygonal form, where the passage is longest in comparison with the preceding solutions and the entrance has a greater width than the exit. In this variant, the flow rate reaches a lower value (0.82 ϕ).

The list of reference numerals and the drawing, together with the articles described or protected in the claims, are an integral part of the disclosure of this Application.

DESCRIPTION OF FIGURES

The figures are described in relation to one another and as a whole. Identical reference numerals denote identical components, and reference numerals having different indices indicate components having the same function.

FIG. 2 shows a detailed representation of the dehumidification process using the device according to the invention;

FIG. 3 shows a sharp-edged nozzle;

FIG. 4 shows a rounded nozzle; and

FIG. 5 shows a cylindrical or polygonal nozzle.

DETAILED DESCRIPTION

Figure 1:
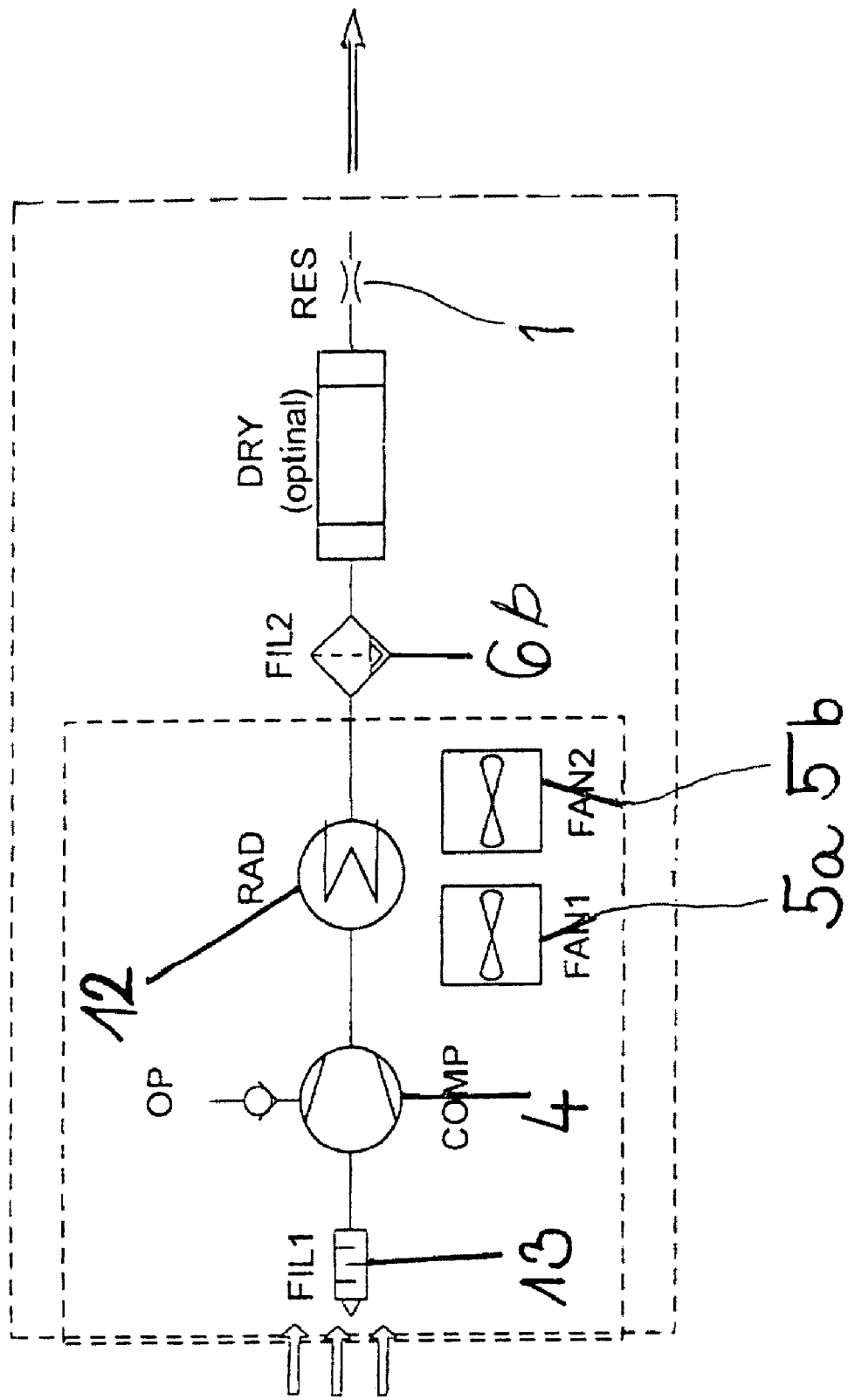
FIG. 1 shows the device according to the invention for generating respirational air, as a block diagram.

FIG. 1 shows a block diagram of a compressor 4 according to the invention. An air intake having a silencer 13 (FILL) is present on the left. Shown thereafter is the compressor 4 with a pressure relief valve 5, to whose exit is connected a radiator 12 onto which cool air can be blown by means of fans 5a, 5b (FAN1, FAN2) and which can thus reduce the temperature of the compressed air.

After the radiator 12 there is a microfilter with water separator 6b (FIL2) which performs the function of removing excess water, which has condensed out of the compressed air, from the air line. The component 1 designated by "RES" comprises the invention, namely the tapering passage which removes moisture from the space after the nozzle according to the invention.

FIG. 2 shows the dehumidification process using the device 1 according to the invention. Before the mixture flowing in the tube 2 and comprising either air or gas and water would reach the tapering passage 9—which may have a nozzle form 3—it is preferably first cooled by fans 5a, 5b in the radiator 12 (FIG. 1). Because of the taper 9 in the nozzle 3, there is a higher pressure and a local increase in the flow rate before it and thereafter a pressure drop, and consequently a further, substantially greater decrease in the temperature in the gas or air mixture. The water condenses out of the gas owing to the local, low temperature in the nozzle 3. The water which has condensed out is entrained by the air stream and can be separated off immediately after the nozzle 3 in a further water separator 6a having a filter 16, before either the gas or the air becomes saturated again owing to the ambient temperature.

FIG. 3-5 show a representation of embodiments of the nozzle 3. The nozzle 3, which is contained as taper 9 of the tube 2, can—as already mentioned further above—have various forms, on which the flow rate and hence the gas or air mixture are dependent.

In the setup according to FIG. 3, the nozzle 3 has a sharp-edged form, in which both the entrance 10 and the exit 11 are of the same size. The passage is furthermore characterized in that its length and width are fairly short. In this possible embodiment, the flow rate is relatively high.

FIG. 4 shows a rounded nozzle form 3 in which the entrance 10 is twice as large as the exit 11. The passage is substantially longer and wider than in the case of FIG. 3. Owing to the above-mentioned properties of the passage, the flow rate in this embodiment is particularly high.

FIG. 5 shows a cylindrical or polygonal nozzle 3 in which both the width and the length of the passage are fairly great. Owing to the polygonal, wide and long form, the flow rate is much slower in relation to the preceding solutions.

LIST OF REFERENCE NUMERALS

1—Device
2 Tube
3—Nozzle
4—Compressor
5—Fan 5a, 5b
6—Water separator
7—Respirational air
8—Moisture content
9—Tapering passage
10—Entrance
11—Exit
12—Radiator
13—Silencer

The invention claimed is:

1. A device for the generation of respirational air, comprising:
    a compressor, from which compressed gas is delivered in a tube;
    a device for cooling; and
    at least one water separator,
    wherein the tube contains a tapering passage after which a first water separator is directly connected, the tapering passage having a cooling effect on the compressed gas when delivered in the tube, wherein a nozzle provides the tapering passage,
    wherein a second water separator is connected to the tube before the tapering passage.

2. The device as claimed in claim 1, wherein the nozzle may have different forms.

3. The device as claimed in claim 1 wherein a further cooling device for the gas is provided in the device before the tapering passage.

4. A method for the generation of respirational air, comprising:
    delivering compressed gas using a compressor;
    passing the gas through a tapering passage in which the gas is cooled; and
    precipitating and separating off water from the gas cooled in the tapering passage by means of a first water separator,
    wherein water which has condensed out of the gas before the compressed gas reaches the tapering passage is separated off in a second water separator.

5. The method as claimed in claim 4, wherein the compressed gas is cooled by at least one fan on the way to the tapering passage.

6. The device of claim 1 where the nozzle has a form selected from the group consisting of: a sharp-edged form, a rounded form, and a cylindrical form.

* * * * *